United States Patent
Vercruysse et al.

(10) Patent No.: US 10,267,998 B2
(45) Date of Patent: Apr. 23, 2019

(54) DEVICE AND METHOD FOR PERFORMING LENS-FREE IMAGING

(71) Applicant: IMEC VZW, Leuven (BE)

(72) Inventors: Dries Vercruysse, Sint-Andries (BE); Pol Van Dorpe, Spalbeek (BE); Xavier Rottenberg, Kessel-Lo (BE); Tom Claes, Merelbeke (BE); Richard Stahl, Rotselaar (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 15/538,572

(22) PCT Filed: Dec. 28, 2015

(86) PCT No.: PCT/EP2015/081302
§ 371 (c)(1),
(2) Date: Jun. 21, 2017

(87) PCT Pub. No.: WO2016/107849
PCT Pub. Date: Jul. 7, 2016

(65) Prior Publication Data
US 2017/0351034 A1    Dec. 7, 2017

(30) Foreign Application Priority Data
Dec. 29, 2014 (EP) .................... 14200424

(51) Int. Cl.
*G02B 6/34* (2006.01)
*G01J 3/28* (2006.01)
(Continued)

(52) U.S. Cl.
CPC .......... *G02B 6/34* (2013.01); *G01N 15/1436* (2013.01); *G01N 15/1484* (2013.01); *G02B 6/12* (2013.01);
(Continued)

(58) Field of Classification Search
USPC ............................................. 385/8
See application file for complete search history.

(56) References Cited

U.S. PATENT DOCUMENTS

| | | | |
|---|---|---|---|
| 4,758,062 A | 7/1988 | Sunagawa et al. | |
| 2008/0030729 A1* | 2/2008 | DiFoggio | G01J 3/02 356/328 |

(Continued)

FOREIGN PATENT DOCUMENTS

| | | |
|---|---|---|
| EP | 2 244 114 A1 | 10/2010 |
| EP | 2 618 130 A1 | 7/2013 |
| EP | 2 657 792 A1 | 10/2013 |

OTHER PUBLICATIONS

PCT International Search Report and Written Opinion, PCT International Application No. PCT/EP2015/081302, dated May 9, 2016, 9 pages.

*Primary Examiner* — Eric Wong
(74) *Attorney, Agent, or Firm* — McDonnell Boehnen Hulbert & Berghoff LLP

(57) ABSTRACT

Embodiments described herein relate to an imaging device, a method for imaging an object, and a photonic integrated circuit. The imaging device includes at least one photonic integrated circuit. The photonic integrated circuit includes an integrated waveguide for guiding a light signal. The photonic integrated circuit also includes a light coupler optically coupled to the integrated waveguide. The light coupler is adapted for directing the light signal out of a plane of the integrated waveguide as a light beam. The imaging device also includes a microfluidic channel for containing an object immersed in a fluid medium. The microfluidic channel is configured to enable, in operation of the imaging device, illumination of the object by the light beam. In (Continued)

addition, the imaging device includes at least one imaging detector positioned for imaging the object illuminated by the light beam.

20 Claims, 17 Drawing Sheets

(51) Int. Cl.
    *G01N 15/14*     (2006.01)
    *G02B 6/12*     (2006.01)
    *G03H 1/04*     (2006.01)

(52) U.S. Cl.
    CPC . *G03H 1/0443* (2013.01); *G02B 2006/12107* (2013.01); *G03H 2001/0447* (2013.01)

(56) References Cited

U.S. PATENT DOCUMENTS

| | | | |
|---|---|---|---|
| 2014/0080729 A1* | 3/2014 | Grego | G01N 21/05 506/9 |
| 2014/0363127 A1 | 12/2014 | Baets et al. | |

* cited by examiner

DEVICE AND METHOD FOR PERFORMING LENS-FREE IMAGING

CROSS-REFERENCE TO RELATED APPLICATION

The present application is a national stage entry of PCT/EP2015/081302 filed Dec. 28, 2015, which claims priority to EP 14200424.1 filed on Dec. 29, 2014, the contents of each of which are hereby incorporated by reference.

FIELD OF THE DISCLOSURE

The disclosure relates to the field of integrated devices for imaging. More specifically it relates to a lens-free imaging device and a related method for imaging an object, e.g. imaging an object under magnification, such as microscopic fluorescence imaging and/or holography.

BACKGROUND

In order to acquire images under magnification, such as in-line holograms, an optical point source may be required. For example, it is known in the art to provide a high quality point source by using a high numerical aperture (NA) objective focused on a pinhole. However, this may require a large optical set-up, which may be expensive and difficult to scale down. Therefore, scalable, micrometer size alternatives may be advantageous. Such scalable alternatives may be used in applications where a large number of objects are to be imaged simultaneously, for example in parallel on-chip holography.

It is known in the art to use a pulled fiber having a very small core diameter to create a high NA light cone with a substantially uniform spherical wavefront. However, a higher level of on-chip integration may be advantageous in semiconductor photonics, e.g. due to the implied cost reduction, manufacturing efficiency and scalability.

SUMMARY

Some embodiments provide efficient lighting of an object to be imaged, for example in microscopic imaging, in-line holographic imaging and/or fluorescence imaging of micrometer scale structures, such as biological cells.

In some embodiments, a large optical set-up, which may be expensive and difficult to scale down, can be avoided.

In some embodiments, a scalable, e.g. a micrometer size, integrated system is provided for lighting an object being imaged.

In some embodiments, a large number of objects can be imaged simultaneously in an efficient manner.

In some embodiments, a high level of on-chip integration can be achieved.

In some embodiments, a substantially uniform spherical wavefront is provided for lighting an object being imaged.

The above may be accomplished by a method and device according to example embodiments.

In a first aspect, the present disclosure relates to an imaging device, e.g. a lens-free imaging device, comprising at least one photonic integrated circuit. This photonic integrated circuit comprises an integrated waveguide for guiding a light signal and a light coupler optically coupled to the integrated waveguide and adapted for directing the light signal out of the plane of the integrated waveguide as a light beam. The imaging device also comprises a microfluidic channel for containing an object immersed in a fluid medium. Thus, the imaging device may comprise a microfluidic channel for transporting the object in a fluid, e.g. a liquid. For example the microfluidic channel may be adapted for containing the fluid medium having the object to be imaged immersed therein, e.g. for transporting the object in a fluid flow of the fluid medium. The microfluidic channel is configured to enable, e.g. adapted for enabling, in operation of the device, illumination of the object by the light beam. The microfluidic channel may, for example, be adapted for this purpose by having a section transparent to the light beam and by being positioned such that the light beam directed out of the plane of the integrated waveguide by the light coupler impinges on the object when this object is present in the transparent section of the microfluidic channel, and such that the light beam, when having interacted with the object, impinges on at least one imaging detector. The imaging device further comprises at least one imaging detector positioned for imaging an object illuminated by the light beam.

In an imaging device according to embodiments of the present disclosure, the light coupler may be a focusing light coupler adapted for focusing the light signal out of the plane of the integrated waveguide as a focused light beam converging in a focal plane. The at least one imaging detector may be positioned for imaging an object illuminated by the focused light beam when this object is positioned in an object imaging location downstream of the focal plane with respect to the direction of propagation of the focused light beam. For example, the object imaging location may correspond to a position in the microfluidic channel, e.g. a central region of the microfluidic channel in an imaging portion of the microfluidic channel. For example, the object imaging location may comprise, or consist of, a point along a central axis of the microfluidic channel.

In an imaging device according to embodiments, the light coupler may be a defocusing light coupler, e.g. a back-focus light coupler, adapted for directing the light signal out of the plane of the integrated waveguide as a diverging light beam diverging from a focal point below the waveguide, e.g. mimicking a diverging light beam emitted by a virtual point source below the waveguide, e.g. on the opposite side of the substrate with respect to the direction to which the light beam is directed out of the plane of the integrated waveguide.

In an imaging device according to embodiments, the focusing light coupler may comprise a pattern of microstructures fabricated in the integrated waveguide. This pattern may be adapted to compensate decay of a light signal propagating in the focusing light coupler. The microstructures may comprise through-holes, pillars and/or cavities, e.g. local depressions or indentations. Such microstructures may have a diameter, in the plane of the waveguide, e.g. a maximal diameter or largest spanning dimension in the plane of the waveguide, that is less than 5 μm, e.g. in the range of 10 nm to 800 nm, e.g. in the range of 20 nm to 500 nm, e.g. in the range of 50 nm to 200 nm.

In an imaging device according to embodiments, the light coupler may comprise a grating coupler, e.g. a focusing grating coupler.

In an imaging device according to embodiments, the at least one photonic integrated circuit may further comprise an optical taper optically coupled to the integrated waveguide and adapted for generating a substantially circular wavefront from the light signal. In an imaging device according to embodiments, the focusing light coupler may be optically coupled to the optical taper and may be adapted for focusing the substantially circular wavefront out of the plane of the integrated waveguide as a focused light beam converging in a focal plane. In an imaging device according to embodiments, the focusing light coupler, e.g. a focusing grating coupler, may have a length of 1 mm or smaller, e.g. 500 µm or smaller, 400 µm or smaller, 300 µm or smaller, 200 µm or smaller, 150 µm or smaller, 100 µm or smaller, 80 µm or smaller, 60 µm or smaller, 50 µm or smaller, 20 µm or smaller, e.g. in the range of 1 µm to 10 µm. The focusing light coupler may furthermore be adapted for generating a focal spot in the focal plane that has a diameter of 10 µm or smaller, e.g. in the range of 1 µm to 5 µm, or even less, e.g. in the range of 0.5 µm to 1.0 µm.

In an imaging device according to embodiments, the at least one photonic integrated circuit may further comprise at least one further light coupler optically coupled to the integrated waveguide and adapted for directing the light signal out of the plane of the integrated waveguide as a light beam. The light coupler and the at least one further light coupler may be positioned such that light beams generated by respectively the light coupler and the at least one further light coupler simultaneously illuminate the object from different angles, for instance coincide and thereby simultaneously illuminate the object from different angles.

An imaging device according to embodiments may comprise a reflective surface, wherein the reflective surface and the at least one imaging detector are positioned such that light from the illuminated object and the light beam is reflected by the reflective surface and detected by the at least one imaging detector after reflection.

An imaging device according to embodiments may furthermore comprise at least one pinhole, positioned in between the at least one photonic integrated circuit and the at least one imaging detector for spatially filtering the light beam, e.g. for spatially filtering the light beam before reaching the object. For example, the at least one pinhole may be positioned at a focal spot of the light beam in the focal plane, e.g. in embodiments where the grating coupler is a focusing grating coupler.

An imaging device according to embodiments may furthermore comprise an excitation waveguide. In an imaging device according to embodiments, the integrated waveguide of the at least one photonic integrated circuit may be optically coupled to the excitation waveguide via a beam splitting means, e.g. a beam splitter, e.g. a waveguide splitter.

In an imaging device according to embodiments, the at least one imaging detector may be adapted for simultaneously imaging a plurality of objects, wherein each object is positioned such that each object is illuminated by a different light coupler. In an imaging device according to embodiments, a plurality of light couplers may be positioned such that a plurality of objects can be illuminated simultaneously. For example, each light coupler may illuminate a corresponding object. For example, an object or plurality of objects may propagate and pass the plurality of light couplers, e.g. when travelling along with a fluid flow in a microfluidic channel.

An imaging device according to embodiments may comprise an input coupler comprising a beam splitting means, e.g. a waveguide splitter, for distributing the light signal over a plurality of integrated waveguides for transmitting the light signal into a corresponding plurality of focusing light couplers for coupling the light signal out of the plane of the integrated waveguide as a corresponding plurality of focused light beams.

In an imaging device according to embodiments, the at least one imaging detector may be adapted for simultaneously imaging a plurality of objects, wherein each object of the plurality of objects is positioned such that each object is illuminated by a corresponding focused light beam emitted by a corresponding light coupler. In an imaging device according to embodiments, a plurality of light couplers may be positioned such that a plurality of objects can be illuminated simultaneously. For example, each light coupler may illuminate a corresponding object, and the at least one imaging detector may be adapted for simultaneously imaging the plurality of objects. For example, an object or plurality of objects may propagate and pass the plurality of light couplers, e.g. when travelling along with a fluid flow in a microfluidic channel.

In an imaging device according to embodiments, the at least one imaging detector may be adapted for acquiring a holographic diffraction image of the object.

In an imaging device according to embodiments, the at least one imaging detector may be adapted for acquiring a fluorescence image of the object.

In an imaging device according to embodiments, the integrated waveguide may be optically coupled to different parts of the light coupler thereby increasing uniformity of the light beam. For example, the integrated waveguide may be optically coupled to a predetermined, discrete number of parts of the light coupler. For example, the integrated waveguide may be optically coupled to the light coupler from opposite sides of the light coupler, e.g. opposite sides lying in the plane of the waveguide. The integrated waveguide may be optically coupled to a plurality of different parts of the light coupler at optical interconnections spaced around the focusing light coupler. For example, the optical interconnections may be spaced apart around the focusing light coupler, e.g. such that each optical interconnection is spaced apart from its neighbors by a predetermined, finite angular interval, e.g. n interval of 360°/n, where n is a finite, natural number greater than 1, for example greater than one and less than 21, e.g. less than 16, e.g. less than 11, e.g. where n is 2, 3, 4 or 5.

An imaging device according to embodiments may comprise an at least partially coherent light source for providing the light signal to the at least one photonic integrated circuit, e.g. such that the at least one imaging detector may acquire a holographic diffraction image of the object.

In a second aspect, the present disclosure also relates to a method for imaging an object. This method comprises coupling a light signal into an integrated waveguide, e.g. into a waveguide integrated in or on a substrate of an integrated circuit device, and generating a light beam from the light signal using a light coupler, whereby the light beam is directed out of the plane of the integrated waveguide. The method further comprises transporting the object by immersing the object in a fluid that flows in a microfluidic channel. The microfluidic channel may for example be configured to enable the illumination of the object by the light beam when the object is transported through the microfluidic channel. The method further comprises illuminating the object using the light beam and imaging the illuminated object.

In a method according to embodiments, generating the light beam may comprise generating a focused light beam from the light signal using a focusing light coupler, e.g. for directing the light signal out of the plane of the integrated waveguide as a focused light beam converging in a focal plane. The method may further comprise illuminating the object with the focused light beam in an object imaging location downstream of the focal plane with respect to the direction of propagation of the focused light beam and imaging the illuminated object.

A method according to embodiments may further comprise forming a light wave having a substantially circular wavefront in the integrated waveguide.

In a method according to embodiments, the generating may comprise focusing the light beam using a focusing light coupler, e.g. generating the light beam from the light signal using the light coupler may comprise introducing the light wave into a focusing light coupler, such as a focusing grating coupler, to couple the light wave out of the plane of the integrated waveguide as a focused beam converging in a focal plane.

In a method according to embodiments, the generating may comprise directing the light signal out of the plane of the integrated waveguide as a diverging light beam diverging from a focal point below the integrated waveguide, e.g. mimicking a diverging light beam emitted by a virtual point source below the waveguide, e.g. on the opposite side of the substrate with respect to the direction to which the light beam is directed out of the plane of the integrated waveguide.

A method according to embodiments may furthermore comprise spatially filtering the light beam in a focal spot thereof thereby obtaining a substantially uniform spherical wave propagating from the focal spot toward the object.

In a method according to embodiments, the steps may be performed in parallel for a plurality of objects using a plurality of different integrated waveguides and a plurality of different light couplers. In a method according to embodiments, the light signal may be coupled into the plurality of integrated waveguides and the imaging may comprise simultaneously imaging a plurality of objects, each object illuminated by a light beam generated by a different light coupler.

In a method according to embodiments, the coupling of the light signal into the integrated waveguide may comprise distributing the light signal over a plurality of integrated waveguides, wherein in each integrated waveguide of the plurality of integrated waveguides a light wave having a substantially circular wavefront is formed. Furthermore, the introducing of the light wave into the focused light coupler may comprise introducing each light wave into a corresponding focusing light coupler for coupling the light wave out of the plane of the integrated waveguide as a corresponding focused beam converging in the focal plane.

A method according to embodiments may further comprise generating at least one further light beam from the light signal using at least one further light coupler, e.g. a further focusing or defocusing light coupler, for directing the light signal out of the plane of the integrated waveguide as the further light beam, and simultaneously illuminating the object with the light beam and the at least one further light beam from different angles.

In a method according to embodiments, the imaging may comprise simultaneously imaging a plurality of objects, each object illuminated by a corresponding focused beam generated by a corresponding light coupler.

In a method according to embodiments, the imaging may comprise acquiring a holographic diffraction image of the object.

In a method according to embodiments, the imaging may comprise acquiring a fluorescence image of the object.

A method according to embodiments may furthermore comprise providing an at least partially coherent light beam for coupling into the integrated waveguide, e.g. as input to an input coupler. The light signal may thus be coupled into the integrated waveguide in the form of the at least partially coherent light beam.

In a method according to embodiments, the light beam may be an at least partially coherent light beam.

A method according to embodiments may furthermore comprise providing an at least partially coherent light beam for coupling into the integrated waveguide.

Particular aspects are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 14 shows a random sampling of scattering microstructure locations from a target distribution of scattering microstructures for use in a light coupler, according to example embodiments of.

Figure 1:
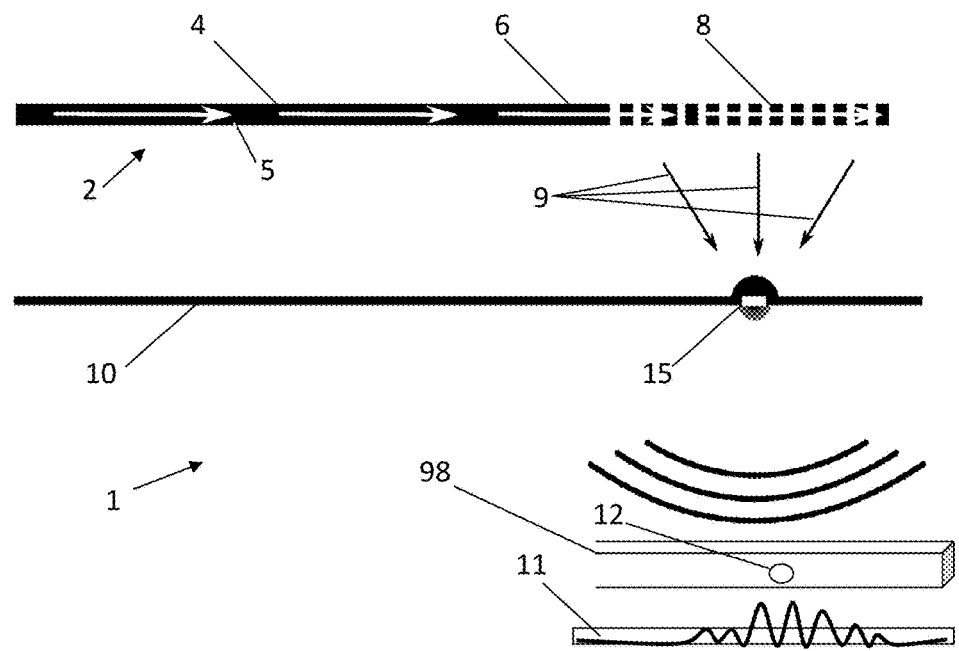
FIG. 1 illustrates an imaging device, according to example embodiments.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of example embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

In the description provided herein, numerous specific details are set forth. However, it is understood that embodiments may be practiced without these specific details. In other instances, well-known methods, structures and techniques have not been shown in detail in order not to obscure an understanding of this description.

Where in embodiments of the present disclosure reference is made to "imaging", reference is made to the process of acquiring a representation or reproduction of an object's spatial properties, e.g. the formation of a two-dimensional image. Such image may comprise a scalar value obtained for a plurality of locations, e.g. over a two-dimensional grid, for example forming a grey-scale image representation, but may also comprise a vector value for a plurality of locations, for example forming a color image representation. For example, such vector value may encode different spectral components, e.g. corresponding to recorded emission intensities for a plurality of different fluorophores. The obtained image may form a direct representation of the structure of the object, for example a magnified optical representation of a microscopic entity, but may also form a more complex representation of the structure of the object, e.g. a holographic interference pattern encoding spatial properties of the object. While imaging may relate to the recording of a static spatial representation of an object, it may also relate to the acquisition of a time series of images, e.g. the acquisition of a video sequence encoding both temporal as well as spatial variations of an optical property of the object under study.

Throughout the description, reference is made to "light". With light in the context of the present disclosure is meant electromagnetic radiation with a wavelength between 375 and 1000 nm, i.e. including visible light, IR radiation, near IR and UV radiation.

Throughout the description reference is made to "a light coupler". This refers to a light propagating region in an integrated circuit, e.g. a region in an integrated waveguide or in contact with an integrated waveguide, e.g. on top of or below an integrated waveguide, where a light dispersing structure for coupling light in and/or out of the integrated circuit is provided, such as a grating. For predetermined incident angles and light frequencies, guided mode resonance may occur, such that the grating couples light into a guided mode of the waveguide. Due to symmetry, this guided mode of the waveguide may also be coupled out of the waveguide along this predetermined angle by the coupler. Specific embodiments relate to devices comprising such a light coupler.

Throughout the description reference is made to "an integrated waveguide". This refers to a light propagating region integrated in or on an integrated circuit, e.g. in an integrated photonic circuit. This may refer to an optical waveguide, such as a planar waveguide, e.g. a dielectric slab waveguide, a strip waveguide, a rib waveguide, a segmented waveguide, a photonic crystal waveguide, a tapered waveguide, or any other light propagating structure known to be suitable for on-chip integration in an integrated circuit.

In a first aspect, the present disclosure relates to an imaging device, e.g. a lens-free imaging device, comprising at least one photonic integrated circuit, e.g. at least one photonic integrated circuit device. This at least one photonic integrated circuit comprises an integrated waveguide for guiding a light signal and a light coupler optically coupled to the integrated waveguide and adapted for directing the light signal out of a plane of the integrated waveguide as a light beam. The imaging device further comprises at least one imaging detector positioned for imaging an object illuminated by the light beam. This object may for example comprise a fluid, e.g. a fluid comprising an immersed biological sample. The imaging device may comprise a microfluidic channel for containing the object to be imaged, e.g. to contain a fluid medium to be analyzed.

The imaging device comprises a microfluidic channel for containing the object immersed in a fluid medium. For example the microfluidic channel may be adapted for containing the fluid medium, e.g. a liquid medium, having the object to be imaged immersed therein, e.g. for transporting the object in a fluid flow of the fluid medium. The microfluidic channel is configured to enable, e.g. adapted for enabling, in operation of the device, illumination of the object by the light beam. The microfluidic channel may be adapted for this purpose by having a section transparent to the light beam and by being positioned such that the light beam directed out of the plane of the integrated waveguide by the light coupler impinges on the object when this object is present in the transparent section of the microfluidic channel, and such that the light beam, having interacted with the object, impinges on at least one imaging detector.

Furthermore, the light coupler may be a focusing light coupler adapted for focusing the light signal out of the plane of the integrated waveguide as a focused light beam converging in a focal plane. Thus, the at least one imaging detector may be positioned for imaging an object illuminated by the focused light beam when this object is positioned in an object imaging location downstream of the focal plane with respect to the direction of propagation of the focused light beam, for example when the object is in an imaging section, e.g. corresponding to the transparent section referred to hereinabove, of the microfluidic channel.

Referring to FIG. 1, an imaging device 1 according to embodiments is shown. Particularly, the imaging device 1 may be a lens-free imaging device, e.g. a device for obtaining a spatial representation of an object by observing a spatial pattern obtained by attenuation, reflection, refraction, diffraction, and/or phase modulation of a light wave incident on the object without requiring an optical lens structure. The device may for example be adapted for imaging the object under magnification, e.g. for obtaining an image of an object under magnification, such as microscopic imaging.

The imaging device 1 comprises a microfluidic channel 98 for containing the object 12 immersed in a fluid medium. For example the microfluidic channel may be adapted for containing the fluid medium, e.g. a liquid medium, having the object to be imaged immersed therein, e.g. for transporting the object in a fluid flow of the fluid medium. The microfluidic channel is configured to enable, e.g. adapted for enabling, in operation of the device, illumination of the object by the light beam. The microfluidic channel may be adapted for this purpose by having a section transparent to the light beam and by being positioned such that the light beam directed out of the plane of the integrated waveguide by the light coupler impinges on the object when this object is present in the transparent section of the microfluidic channel, and such that the light beam, having interacted with the object, impinges on at least one imaging detector.

Figure 2:
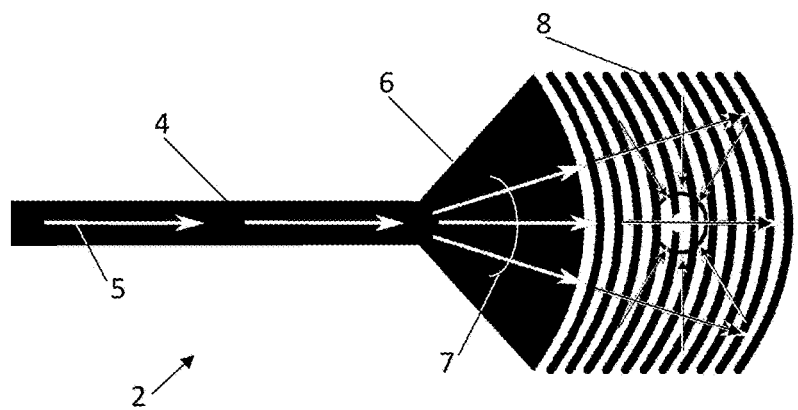
FIG. 2 shows an exemplary integrated photonic device in an imaging device, according to example embodiments.

This imaging device 1 comprises at least one photonic integrated circuit 2. A photonic integrated circuit 2 according to embodiments, e.g. as shown in FIG. 2 in a transverse projection with respect to a substrate plane thereof, comprises an integrated waveguide 4 for guiding an excitation light signal 5. For example, the photonics integrated circuit device 2 may comprise a substrate suitable for integrated photonic circuit processing, e.g. a silicon-on-insulator (SOI) substrate, in or on which the integrated waveguide 4 is provided. In some embodiments, a light source, e.g. providing a focused light beam having a point-like focus, can be provided using integrated photonic processing technology. In some embodiments, a plurality, e.g. a large number, of such light sources can be provided on a single substrate, thus providing a low-cost and efficient to manufacture lighting source for parallel imaging of a plurality of objects.

For example, the imaging device 1 may comprise a light source, e.g. an at least partially coherent light source, for providing the excitation light signal 5 to the at least one photonic integrated circuit 2. For example, such light source may comprise a laser or light-emitting diode (LED) to provide at least partially coherent light with a limited bandwidth for coupling to the integrated waveguide on the photonic integrated circuit. In some embodiments, holographic imaging can be provided of an object in an efficient and low-cost manner, e.g. holographic imaging of a large number of objects simultaneously.

Figure 29:
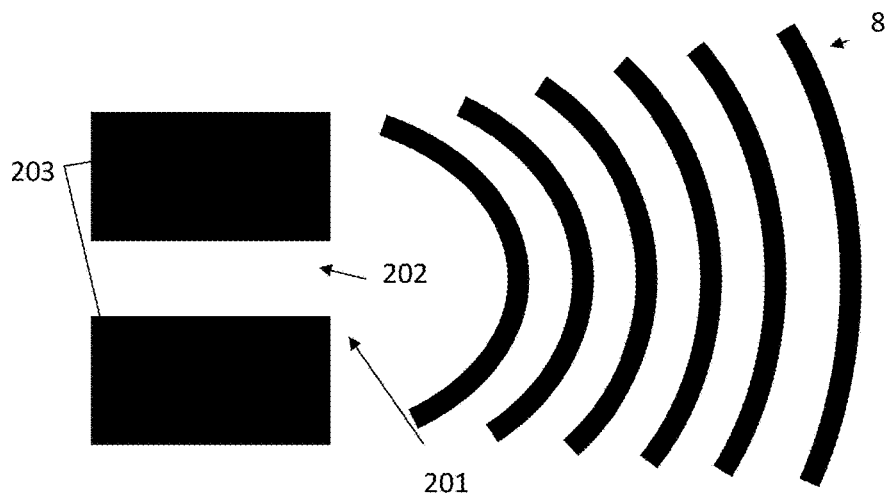
FIG. 29 illustrates a first integrated waveguide in an imaging device, according to example embodiments.
Figure 30:
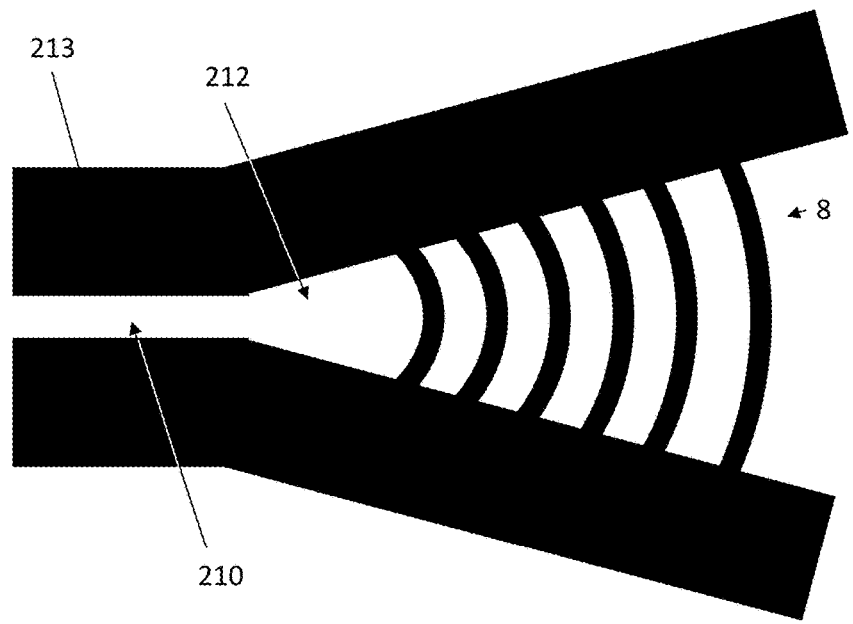
FIG. 30 illustrates a second integrated waveguide in an imaging device, according to example embodiments.

For example, in some embodiments, the integrated waveguide may comprise a ridge or rib waveguide 201, e.g. a light conducting channel defined by a slab of high refractive index material 202 arranged between regions of low refractive index material 203. The light coupler 8 may for example be provided in a slab of high refractive index material optically coupled to the ridge or rib waveguide 201. An example of such embodiment is shown in FIG. 29. In some embodiments, the integrated waveguide may comprise a tapered waveguide 210, e.g. a light conducting channel defined by a tapered region of high refractive index material 212 arranged between regions of low refractive index material 213. An example of such embodiment is shown in FIG. 30. For example, the light coupler 8 may be formed in the tapered section of such tapered waveguide 210.

Figure 31:
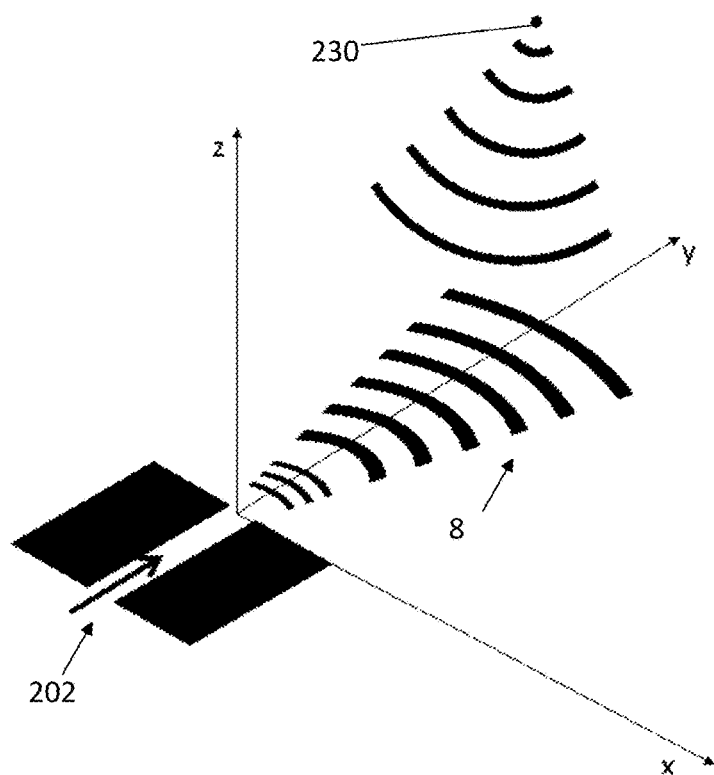
FIG. 31 illustrates aspects of an imaging device, according to example embodiments.

FIG. 31 furthermore shows an example illustrating aspects of such embodiment. An excitation wave having wavelength λ propagates through the waveguide 202. A cylindrical phase front in the waveguide propagates into the light coupler 8. Then, the light signal is coupled out of the plane of the waveguide, e.g. out of the xy plane, towards a focus point 230, e.g. at $(0,f_y,f_z)$. For example, an out-of-plane spherical phase front propagates from the light coupler 8 in a medium with refractive index $n_{top}$ towards the predetermined focus point, where for example a pinhole may be placed in accordance with embodiments. Thus, light coming from the waveguide 202, e.g. a ridge or a rib waveguide, may be coupled to a planar waveguide region, where it diffracts with a cylindrical phase front. In order to couple this light out-of-plane and focus it in a desired focus point with coordinates $(0,f_y,f_z)$, a light coupler may have grating lines that are shaped accordingly. For example, one possible shape to accomplish this is defined by:

$$n_{eff,planar}\sqrt{x^2+y^2}+n_{top}\sqrt{x^2+(y-f_y)^2+f_z^2}=my+n_{top}\sqrt{f_y^2+f_z^2}$$

where m is an integer number that corresponds to different grating lines.

The at least one photonic integrated circuit may comprise an excitation waveguide. The integrated waveguide of the at least one photonic integrated circuit may be optically coupled to the excitation waveguide via a beam splitting means, e.g. a waveguide splitter. The at least one photonic integrated circuit may comprise an input coupler adapted for coupling the excitation light signal 5 into the integrated waveguide. When the device comprises multiple integrated waveguides coupled to the excitation waveguide via the beam splitting means, e.g. the waveguide splitter, the excitation waveguide may comprise an input coupler adapted for coupling the excitation light signal 5 into the excitation waveguide. For example, an imaging device according to embodiments may comprise an input coupler comprising a beam splitting means, e.g. a waveguide splitter, for distributing the light signal over a plurality of integrated waveguides having a corresponding plurality of optical tapers for transmitting the light signal into a corresponding plurality of focusing light couplers for coupling the light signal out of the plane of the integrated waveguide as a corresponding plurality of focused light beams.

In an imaging device according to embodiments, the at least one photonic integrated circuit may further comprise a free propagation region 14 optically coupled to the integrated waveguide 4. The free propagation region 14 is adapted such that a large, e.g. circular, wavefront 13 is generated in the free propagation region, from a light signal 5 propagating in the integrated waveguide 4. The free propagation region 14 may be a large surface optically coupled to the integrated waveguide 4. In some embodiments, the material of the free propagation region 14 has the same refractive index as the refractive index of the integrated waveguide 4. The free propagation region 14 may be a slab fabricated from the same material as the integrated waveguide 4. In such an embodiment, the light coupler 8, e.g. a focusing light coupler such as a focusing grating coupler, may be positioned in the free propagation region 14 such that the generated wavefront in the free propagation region 14 can be coupled out of the free propagation region 14 using the light coupler 8. For example, the light coupler 8 may be etched in the free propagation region 14.

Figure 27:
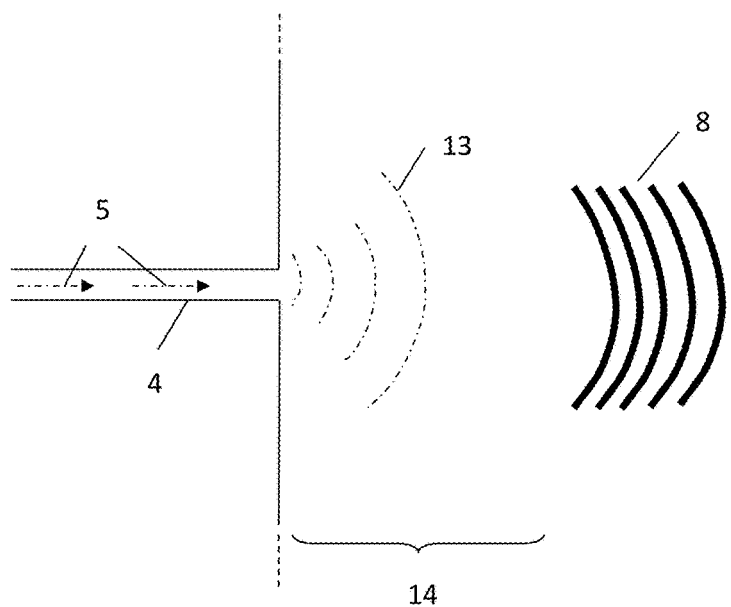
FIG. 27 illustrates parts of an imaging device comprising a free light propagation region, according to example embodiments.

In some embodiments, by using a free propagation region 14, improved, e.g. optimized, illumination of the light coupler 8 can be achieved, thereby contributing to efficient out-coupling of light by the light coupler 8. Such an embodiment is illustrated in FIG. 27.

The photonic integrated circuit 2 may further comprise an optical taper 6 optically coupled to the integrated waveguide 4 and adapted for generating a widened wavefront 7 from the light excitation signal 5. The optical taper may create an in plane two-dimensional spherical wavefront. For example a portion of the waveguide may be adapted in shape to form a tapered section for transmitting the light signal as a light wave having a substantially circular wavefront into the light coupler 8, e.g. into a focusing light coupler such as a focusing grating coupler.

Alternatively, the optical taper may be adapted for generating a substantially quasi-planar wavefront, e.g. a planar wavefront, from the light signal 5. The optical taper may create an in plane two-dimensional wavefront. For example a portion of the waveguide may be adapted in shape to form a tapered section for transmitting the light signal as a light wave having a substantially planar wavefront into the light coupler 8, e.g. into a focusing light coupler.

The photonic integrated circuit 2 further comprises a light coupler 8, e.g. a grating coupler or other coupler for coupling light out of the integrated circuit 2, optically coupled to the integrated waveguide and adapted for directing the light signal out of the plane of the integrated waveguide as a light beam. In an imaging device according to embodiments, the light coupler may be a focusing light coupler, e.g. a focusing grating coupler or other coupler for coupling light out of the integrated circuit 2 in a focused beam, adapted for focusing the light signal out of the plane of the integrated waveguide as a focused light beam converging in a focal plane. For example, the focusing grating coupler may be adapted for focusing a substantially circular or planar wavefront 7, e.g. the light wave having a substantially circular or planar wavefront 7, out of the plane of the planar waveguide, e.g. out of the plane of a substrate of the photonic integrated circuit.

In an imaging device according to embodiments, the light coupler may be a defocusing light coupler, e.g. a defocusing grating coupler or other coupler for coupling light out of the integrated circuit 2 in a divergent beam, adapted for directing the light signal out of the plane of the integrated waveguide as a diverging light beam. Thus, in an imaging device according to embodiments, the light coupler may be designed such that the light coupler has a virtual focal point 16 on one side of the light coupler while a light wavefront is generated on the other side of that light coupler. For example, the light coupler may comprise different structures, wherein each structure or each group of structures is designed to out-couple light to a different direction. The ensemble of structures may thus conjointly create a quasi-circular light wavefront on one side of the light coupler, e.g. on one side of the plane of the integrated waveguide, wherein the virtual focal point 16 of that wavefront is located on the other side of the grating coupler, e.g. on the opposite side of the plane of the integrated waveguide.

Figure 28:
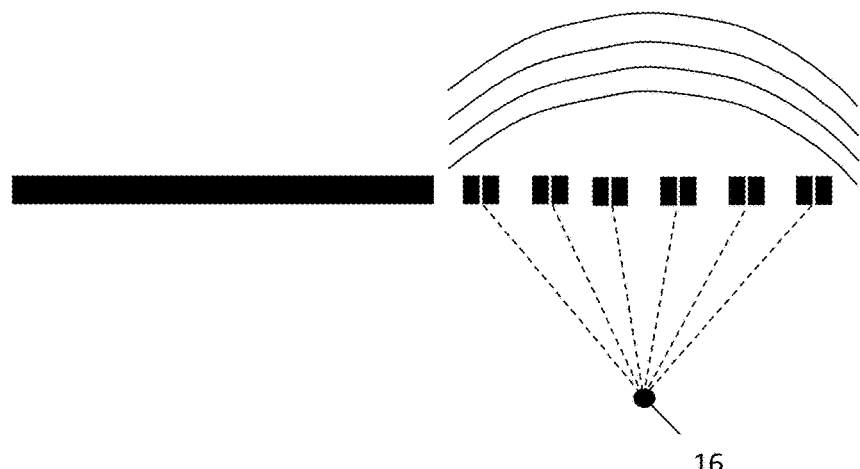
FIG. 28 illustrates parts of an imaging device comprising a defocusing light coupler, according to example embodiments.

In some embodiments, objects can be positioned close to the light coupler, which also contributes to compactness of the device. Such an embodiment is illustrated in FIG. 28.

In a light coupler, such as a grating coupler, for out-coupling of a light signal, that light signal, fed by a waveguide, may decay while it propagates through the light coupler. This gives rise to a non-uniform distribution of light, which may be disadvantageous for illuminating objects in particular applications. In some embodiments, the integrated waveguide may be optically coupled to different parts of the light coupler, thereby increasing uniformity of a generated light beam. For example, the integrated waveguide may be optically coupled to one part of the light coupler and the integrated waveguide may be optically coupled to another part of the light coupler. By coupling the integrated waveguide at different locations to the light coupler, the problem of light decay inside the light coupler is solved and a light beam with uniformity can be generated. The phase difference between different light signals arriving at the light coupler, e.g. between light propagating into the coupler at the different locations, may be substantially zero, e.g. may be zero, e.g. may be as small as achievable within manufacturing tolerances and cost constraints.

For example, the integrated waveguide may be optically coupled to a predetermined, discrete and finite number of parts of the light coupler. For example, the integrated waveguide may be optically coupled to the light coupler from opposite sides of the light coupler, e.g. opposite sides lying in the plane of the waveguide. The integrated waveguide may be optically coupled to a plurality of different parts of the light coupler at optical interconnections spaced around the focusing light coupler. For example, the optical interconnections may be spaced apart around the focusing light coupler, e.g. such that each optical interconnection is spaced apart from its neighbors by a predetermined, finite angular interval, e.g. an interval of 360°/n, where n is a finite, natural number greater than 1.

In an embodiment, the integrated waveguide may be optically coupled to a first and a second waveguide. Thus, a light signal propagating in the integrated waveguide will optically split and propagate through the first and the second waveguide. The first waveguide may be optically coupled to one side, e.g. one end, of the light coupler, and the second waveguide may be optically coupled to another side, e.g. the other end, of the same light coupler. By splitting the integrated waveguide into two waveguides, the same light signal propagating through the waveguide can be fed twice to the light coupler at different locations to compensate for, or at least reduce the effect of, decay of the light signal in the light coupler. In some embodiments, the phase difference between both light signals arriving at the light coupler is substantially zero. Thus the first and the second waveguide may be fabricated such that that the phase difference between light signals arriving at the light coupler is substantially zero, e.g. is equal to zero, e.g. is equal to zero within a predetermined tolerance range, e.g. within manufacturing tolerances.

In an embodiment, the integrated waveguide may be optically coupled to the light coupler at a plurality of locations of the light coupler for increasing uniformness of the light beam even further. For example, the integrated waveguide may be optically coupled to a plurality of waveguides, e.g. to three, four, five, six or even more waveguides. Thus, a light signal propagating in the integrated waveguide will optically split and propagate through each of this plurality of waveguides. The plurality of waveguides may be optically coupled to a plurality of locations on the grating coupler.

The focusing light coupler may be adapted for focusing the substantially circular or planar wavefront 7 out of the plane of the waveguide as a focused light beam 9 converging in a focal plane 10. For example, the focusing light coupler may be a focusing grating coupler having a chirped and curved grating pattern adapted to out-couple the guided light signal having a substantial circular or planar wavefront into a spherical wave focusing in free space.

Alternatively, the focusing light coupler may comprise a pattern of microstructures which are fabricated, e.g. patterned, in the integrated waveguide. The microstructures may comprise through-holes, pillars and/or cavities, e.g. local depressions or indentations. Such microstructures may have a diameter, in the plane of the waveguide, e.g. a maximal diameter or largest spanning dimension in the plane of the waveguide, that is less than 5 µm, e.g. in the range of 10 nm to 800 nm, e.g. in the range of 20 nm to 500 nm, e.g. in the range of 50 nm to 200 nm.

The microstructures may be at least partly fabricated, e.g etched, in the waveguide. The microstructures may be through-holes in the waveguide. The through-hole may have any suitable shape, e.g. rectangular. The microstructures may also be a combination of different types of microstructures which are fabricated into the waveguide, for example microstructures which are fully (e.g. a through-hole) or partly (e.g. an indentation) fabricated into the waveguide. The pattern may be a regular pattern. According to embodiments of the invention, the pattern may be configured to compensate for a decay of the light signal as the light signal propagates through the grating coupler when being received from the waveguide. This configured pattern ensures that the generated light cone has an increased uniformity which permits the use of larger pinholes compared to when regular patterns are used. In some embodiments, the energy of light used to illuminate objects is increased giving rise to better illumination of objects. Thus, the focusing light coupler may be a focusing light coupler as described further hereinbelow in detail.

Figure 6:
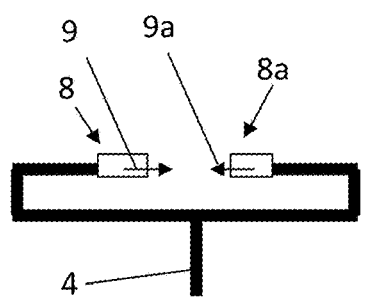
FIG. 6 illustrates an imaging device, according to example embodiments.
Figure 7:
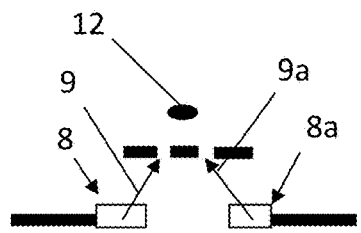
FIG. 7 illustrates an imaging device, according to example embodiments.

According to an embodiment, different light couplers may be used to simultaneously illuminate an object from different angles. The different light couplers may be connected to the same integrated waveguide which provides the light signal to all the light couplers. For example, the at least one photonic integrated circuit 2 may comprise at least one further light coupler 8a which is optically coupled to the integrated waveguide 4. The at least one further light coupler 8a may be adapted for directing the light signal 5 out of the plane of the integrated waveguide 4 as a light beam 9a. The light coupler 8 and the at least one further light coupler 8a are positioned such that generated light beams by the light coupler 8 and the at least one further light coupler 8a coincide and thereby simultaneously illuminate the object from different angles. Such an embodiment is illustrated in FIG. 6 and FIG. 7. In some embodiments, illumination of an object from different angles allows the recording of 3D information of the object. By incorporating the 3D information to identify the object, a higher accuracy can be achieved.

In another embodiment, each light coupler may have its own integrated waveguide that feeds a light signal into that light coupler and wherein different light couplers are positioned to illuminate an object from different angles. For example, the at least one photonic integrated circuit may further comprises at least one other integrated waveguide for guiding a light signal, and at least one other light coupler optically coupled to the at least one other integrated waveguide. The other light coupler may be adapted for directing the light signal out of the plane of the at least one other waveguide as another light beam. The light coupler and the other light coupler may be positioned such that generated light beams by the light coupler and the other light coupler coincide and thereby simultaneously illuminate the object from different angles.

Techniques are known in the art to design and fabricate a focusing light coupler for a device according to embodiments, e.g. a suitable grating pattern may be created using electron beam processing techniques onto a substrate of the integrated photonics device 2. The periodicity of the focusing grating coupler may vary as function of location such that the out-coupled light is focused in a single concentrated spot in the focal plane. A high numerical aperture and small spot size may be achieved by a sufficiently large grating and a short focal distance. For example, a grating of about 10 µm to 100 µm may provide a spot of 5 µm to 100 µm.

For example, the focusing grating coupler may have a length in the range of 10 µm to 1000 µm and may be adapted for generating a focal spot in the focal plane that has a diameter in the range of 5 µm to 100 µm. The focusing grating coupler may have a length of 500 µm or smaller, e.g. in the range of 1 µm to 100 µm. The focusing grating coupler may furthermore be adapted for generating a focal spot in the focal plane that has a diameter of 10 µm or smaller, e.g. in the range of 1 µm to 5 µm, or even less, e.g. in the range of 0.5 µm to 1.0 µm.

The imaging device 1 further comprises at least one imaging detector 11, such as a CMOS image detector, positioned for imaging an object 12 illuminated by the light beam 9. The at least one imaging detector 11 may for example be adapted for imaging the object when the object is positioned downstream of a focal plane with respect to the propagation direction of the light beam, in embodiments where the generated light beam is a focused light beam. Furthermore, the imaging device may comprise other parts such as known in the art for performing image acquisition, digitization and/or transmission and/or storage of the image. The imaging device may also comprise processing means, e.g. a processor such as an application specific integrated circuit device, adapted for performing image processing operations, such as for example image filtering, image transformation, pattern recognition and/or image compression.

Figure 5:
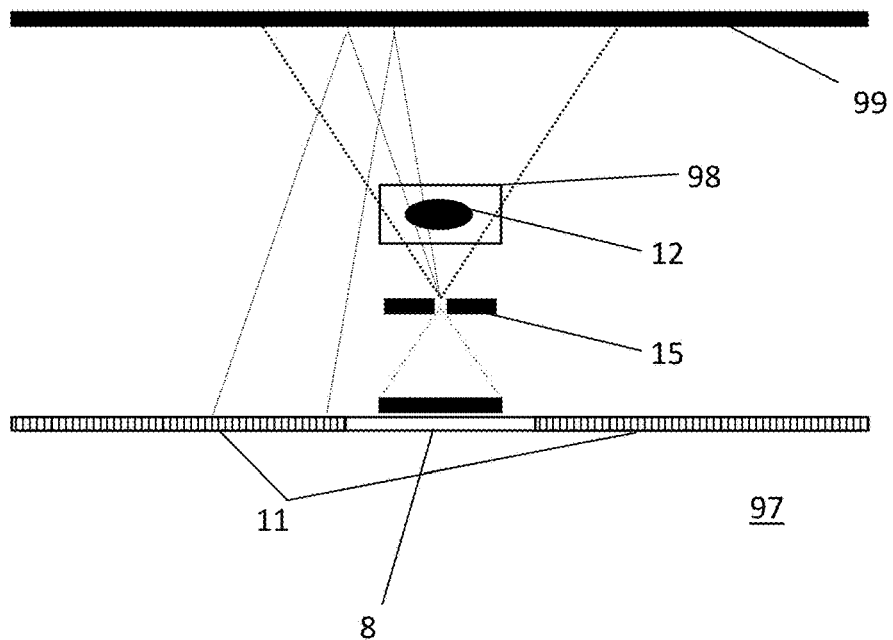
FIG. 5 illustrates an embodiment in which fluid comprising an immersed biological sample contained in a microfluidic channel is imaged, according to example embodiments.

The object 12 may for example comprise a fluid, e.g. a fluid comprising an immersed biological sample, contained in a microfluidic channel 98, e.g. as illustrated in FIG. 5.

The at least one imaging detector may for example be adapted for acquiring a holographic diffraction image of the object 12.

The at least one imaging detector 11 may be adapted for acquiring a fluorescence image of the object 12. For example, the imaging device 1 may comprise at least one spectral filter adapted for spectrally isolating a fluorescence wavelength of a fluorescent agent, e.g. for band-pass filtering the light incident on the at least one imaging detector such as to reject or substantially attenuate wavelengths outside a pass-band comprising the fluorescence wavelength.

The photonic integrated circuit 2 may further comprise at least one pinhole collimator 15, e.g. at least one pinhole 15, positioned in between the photonic integrated circuit 2 and the at least one imaging detector 11 for spatially filtering the light beam 9, e.g. for filtering the light beam before reaching the object. For example, the wavefront of a focused light beam may be cleaned up by a pinhole at the focal plane, e.g. the pinhole collimator may implement a low spatial frequency band pass filter. The at least one pinhole collimator may thus be positioned in the focal plane for spatially filtering the focused light beam.

Figure 3:
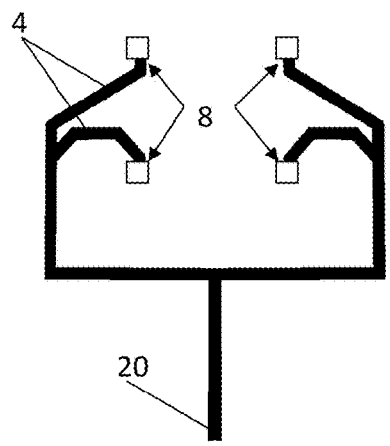
FIG. 3 shows an integrated photonic device for use in an imaging device, according to example embodiments.

The at least one imaging detector 11 may be adapted for simultaneously imaging a plurality of objects 12, wherein each object of the plurality of objects is positioned such as to allow illumination of each object by a corresponding light beam emitted by a corresponding light coupler, e.g. when each object is positioned downstream of the focal plane with respect to the propagation direction of a corresponding focused beam emitted by a corresponding light coupler. Thus, an excitation waveguide, e.g. a single excitation waveguide, may be split in a plurality of integrated waveguides, e.g. via an optical beam-splitting means, connecting to corresponding tapers and corresponding focusing light couplers in order to divide and guide the light to a plurality of objects. For example, FIG. 3 shows a photonic integrated device 2 according to embodiments comprising an excitation waveguide 20, e.g. adapted for coupling the light signal into the photonic integrated device 2 and a plurality of integrated waveguides 4 for guiding the light signal to four spots. For example, each focused light beam provided by the plurality of focusing light couplers 8 may generate a point source which can for example be used to illuminate an object. After illumination, a hologram of the object may be recorded.

Furthermore, an imaging device according to embodiments may comprise a reflective surface, wherein the reflective surface and the at least one imaging detector are positioned such that light from the illuminated object and the light beam is reflected by the reflective surface and detected by the at least one imaging detector after reflection.

Referring to FIG. 5, an example embodiment is shown, in which the imaging device comprises such reflective surface 99, e.g. a mirror or a metal layer, having a suitable reflection factor, deposited on a substrate. In some embodiments, the at least one integrated circuit 2 and the at least one imaging detector 11 can be integrated on a single substrate 97, e.g. on a single integrated photonics chip. A blind spot in the imaging detector 11 may for example be used to implement the integrated photonics. In some embodiments, the integrated photonics and imaging detector may be fabricated using CMOS compatible processing steps. This simplifies processing and reduces the manufacturing cost of the device. Furthermore, a pinhole collimator 15, e.g. a layer, such as a metallic layer, having a pinhole aperture provided therein, may be provided in between the micro-fluidic channel 98 and the substrate 97. Fabrication of such a device is explained in the next paragraph.

The pinhole collimator 15, e.g. the pinhole 15, may be provided on the substrate 97, e.g. over a transparent spacing layer, e.g. an oxide layer, arranged over the substrate 97. A microfluidic channel 98 may also be provided on the same substrate 97, e.g. a second transparent spacing layer, e.g. an oxide layer, may be provided over the pinhole collimator 15, in which a microfluidic channel 98 is formed. Likewise, the reflective surface may be provided as a layer over the microfluidic channel 98, e.g. spaced away from the microfluidic channel 98 by a third transparent spacing layer, e.g. an oxide layer. This may allow an easy alignment in operation, e.g. components which may be highly sensitive to alignment errors can be integrated on a single substrate.

In a second aspect, the present disclosure also relates to a method for imaging an object. This method comprises coupling a light signal into an integrated waveguide, e.g. into an integrated waveguide in or on a substrate, and generating a light beam from the light signal using a light coupler, wherein the light beam is directed out of the plane of the integrated waveguide. The method further comprises transporting the object by immersing the object in a fluid that flows in a microfluidic channel. The microfluidic channel may for example be configured to enable the illumination of the object by the light beam when the object is transported through the microfluidic channel. The method further comprises illuminating the object using the light beam and imaging the illuminated object. Details of a method according to embodiments will also be understood by the skilled person in the light of the description hereinabove relating to an imaging device according to embodiments. For example, a method according to embodiments or a portion thereof may be carried out in practice by a device according to embodiments or a corresponding portion thereof.

Figure 4:
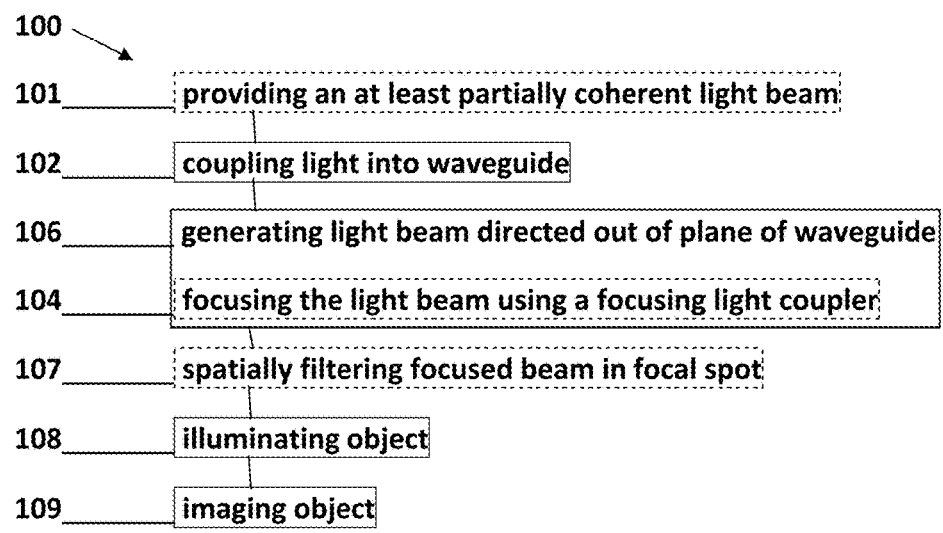
FIG. 4 illustrates a method, according to example embodiments.

An example method 100 for imaging an object according to embodiments is shown in FIG. 4. This method 100 comprises coupling 102 a light signal into an integrated waveguide, e.g. an integrated waveguide in or on a substrate such as an integrated photonic circuitry substrate. The coupling 102 of the light signal into the integrated waveguide may comprise distributing the light signal over a plurality of waveguides. For example, the light signal may be distributed such that in each integrated waveguide of the plurality of integrated waveguides a light wave having a substantially circular wavefront is formed.

A method according to embodiments may furthermore comprise providing 101 an at least partially coherent light beam, e.g. for coupling into the integrated waveguide, e.g. as input to an input coupler. The light signal may thus be coupled into the integrated waveguide in the form of the at least partially coherent light beam. The method 100 may also comprise forming a light wave having a substantially circular or planar wavefront in the integrated waveguide, e.g. to feed into a light coupler. e.g. a focusing light coupler such as for example a focusing grating coupler.

The method also comprises generating 106 a light beam from the light signal using a light coupler, such that the light beam is directed out of the plane of the integrated waveguide. In a method according to embodiments, the generating 106 may comprise focusing 104 the light beam using a focusing light coupler, e.g. generating the light beam from the light signal using the light coupler may comprise introducing the light wave into a focusing light coupler to couple the light wave out of the plane of the waveguide as a focused beam converging in a focal plane.

In a method according to embodiments, the generating 106 may comprise generating the light beam using a defocusing light coupler, e.g. generating the light beam from the light signal using the light coupler may comprise introducing the light wave into a defocusing light coupler to couple the light wave out of the plane of the waveguide as a diverging beam, e.g. diverging from a virtual point source below the plane of the waveguide, e.g. coupling the light out of the plane of the waveguide as a diverging beam in a direction opposite of the side where this virtual point source lies with respect to the plane of the waveguide.

A method according to embodiments may furthermore comprise spatially filtering 107 the light beam in a focal spot thereof to obtain a substantially uniform spherical wave, e.g. a uniform spherical wave, propagating from the focal spot toward the object.

In a method according to embodiments, the steps, e.g. the coupling 102 of light into the waveguide, the generating 106 of the light beam, the illuminating 108 of the object and/or the imaging 109 of the object, may be performed in parallel for a plurality of objects using a plurality of different waveguides and a plurality of different light couplers. In a method according to embodiments, the light signal may be coupled into the plurality of integrated waveguides and the imaging may comprise simultaneously imaging a plurality of objects, each object illuminated by a light beam generated by a different light coupler.

In a method according to embodiments, the coupling of the light signal into the integrated waveguide may comprise distributing the light signal over a plurality of waveguides, wherein in each integrated waveguide of the plurality of waveguides a light wave having a substantially circular or planar wavefront is formed. Furthermore, the introducing of the light wave into the focused light coupler may comprise introducing each light wave into a corresponding focusing light coupler for coupling the light wave out of the plane of the waveguide as a corresponding focused beam converging in the focal plane.

The method 100 further comprises illuminating 108 the object using the light beam and imaging 109 the illuminated object. Furthermore, the method 100 may also comprise simultaneously imaging a plurality of objects, each object illuminated by a corresponding light beam generated by a corresponding light coupler. Imaging 109 of the illuminated object may comprise acquiring a holographic diffraction image and/or acquiring a fluorescence image of the object.

Embodiments may comprise or otherwise relate to a focusing light coupler comprising a pattern of microstructures that are fabricated, e.g. patterned or formed, in the waveguide. The microstructures may be at least partly fabricated, e.g. etched, in the waveguide. The microstructures may comprise through-holes in the waveguide. Such a through-hole may have any suitable shape, e.g. a rectangular shape. The microstructures may also comprise a combination of different types of microstructures fabricated into the waveguide, for example microstructures which are fully (e.g. a through-hole) or partly (e.g. an indentation) fabricated into the waveguide. For example, a microstructure may be fabricated in the waveguide such as to fully traverse the waveguide, e.g. a through-hole, or a microstructure may be fabricated in the waveguide such as to extend into the waveguide, e.g. an indentation. The pattern may be a regular pattern. According to embodiments, the pattern may be configured to compensate for a decay of the light signal as the light signal propagates through the light coupler when being received from the waveguide. This configured pattern may ensure that the generated light cone has an increased uniformity that permits the use of larger pinholes compared to when regular patterns are used. In some embodiments, the energy of light used to illuminate objects is increased giving rise to better illumination of objects. For example, in order to provide a uniform out-coupling of light, the microstructures may form scattering centers. Thus, instead of using a fully formed focusing grating coupler comprising a plurality of curved grating lines, the microstructures may be provided on the grating lines, e.g. at locations substantially corresponding to locations on the grating lines of a fully formed focusing grating coupler with substantially identical light coupling properties as the light coupler at hand, in accordance with a density distribution adapted for locally controlling the out-coupled light intensity. In some embodiments, the light coupler may have microstructures positioned on the light coupler in accordance with a density distribution that is a discrete sampling approximation of a continuous density distribution adapted for, e.g. optimized for, providing a predetermined target out-coupled light power distribution. In another aspect, the present disclosure may also relate to a method for designing such focusing light coupler and/or a method for manufacturing such focusing light coupler.

Figure 8:
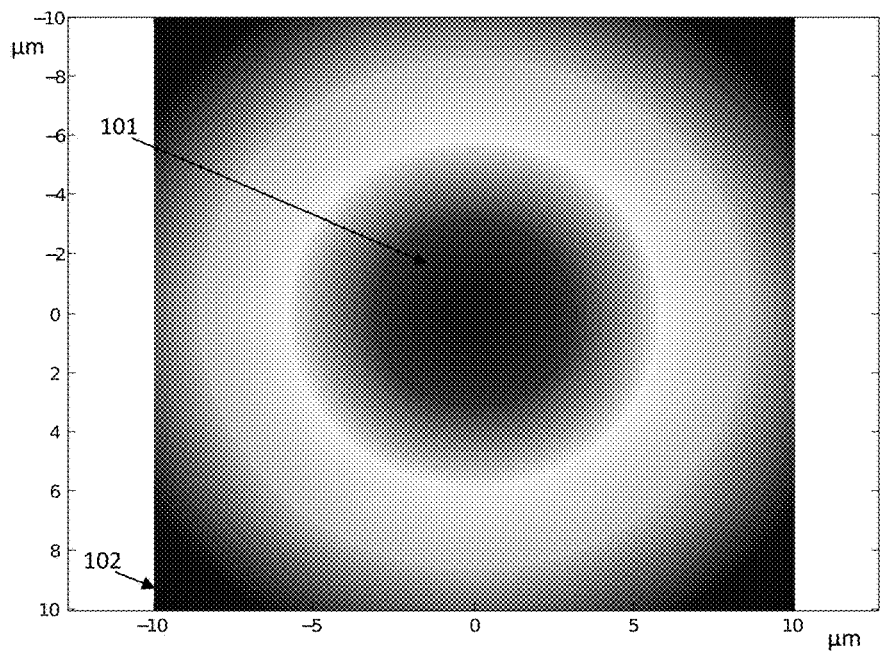
FIG. 8 shows an out-coupling power distribution for providing an approximation of a point source, for illustrating aspects according to example embodiments.

Referring to FIG. 8, an out-coupling power distribution R is shown that could provide an approximation of a point source. For example, in a central area 101 of the plane in which the light coupler is to be formed, the out-coupled power can be lower than in a peripheral area 102, e.g. in order to account for a larger distance for the out-coupled wave to travel before reaching the focal point above the central area 101, e.g. to overcome an inverse squared distance loss factor. This out-coupling power distribution R(r) can be related to the power distribution P in the light coupler, e.g. by the mathematical model:

$$\frac{dP(r)}{dr} = -\frac{1}{r}P(r) - R(r);$$

Figure 9:
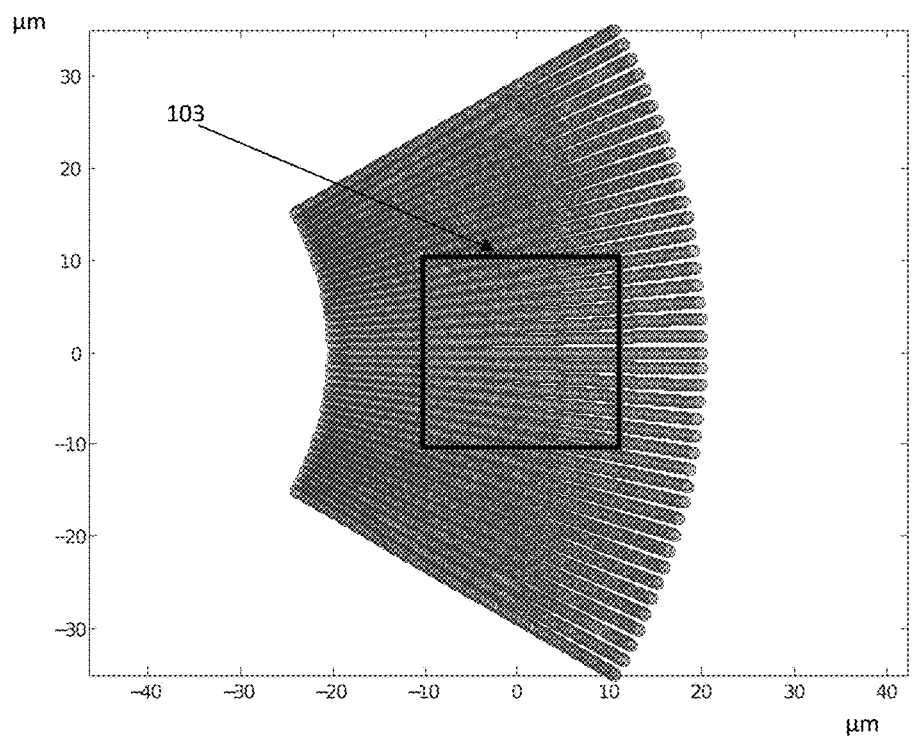
FIG. 9 shows a grating coupler, according to example embodiments.
Figure 10:
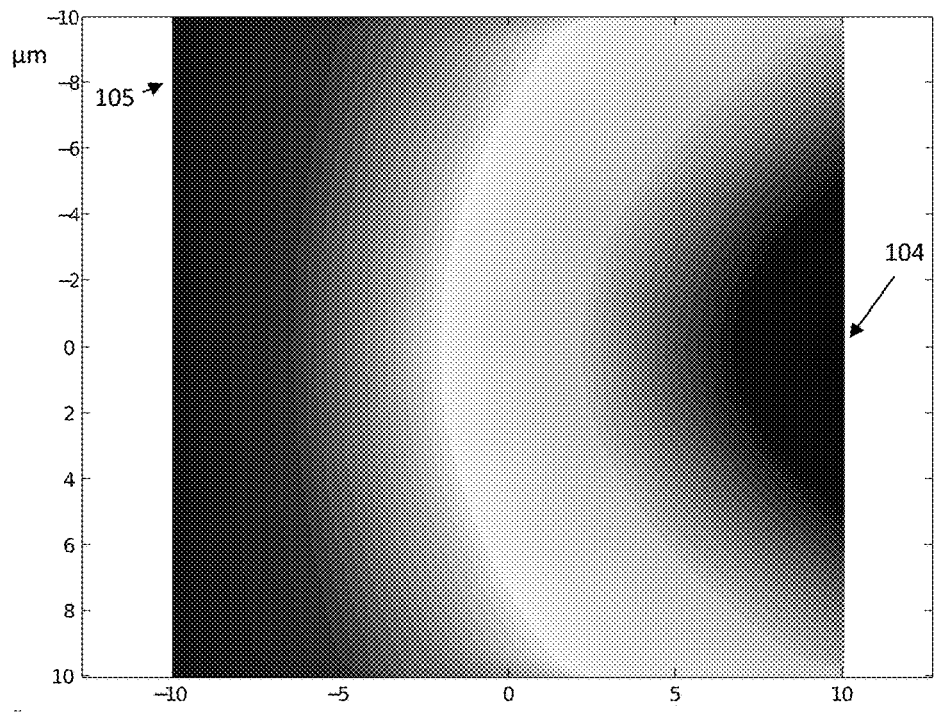
FIG. 10 shows a target power distribution of light propagating through a grating coupler according to example embodiments.
Figure 11:
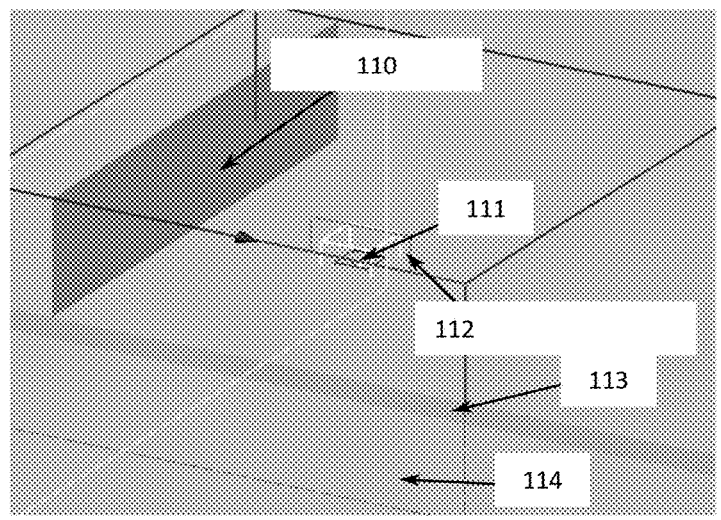
FIG. 11 shows a simulation model for determining the scattering cross-section of a microstructure for use in a light coupler, according to example embodiments.
Figure 12:
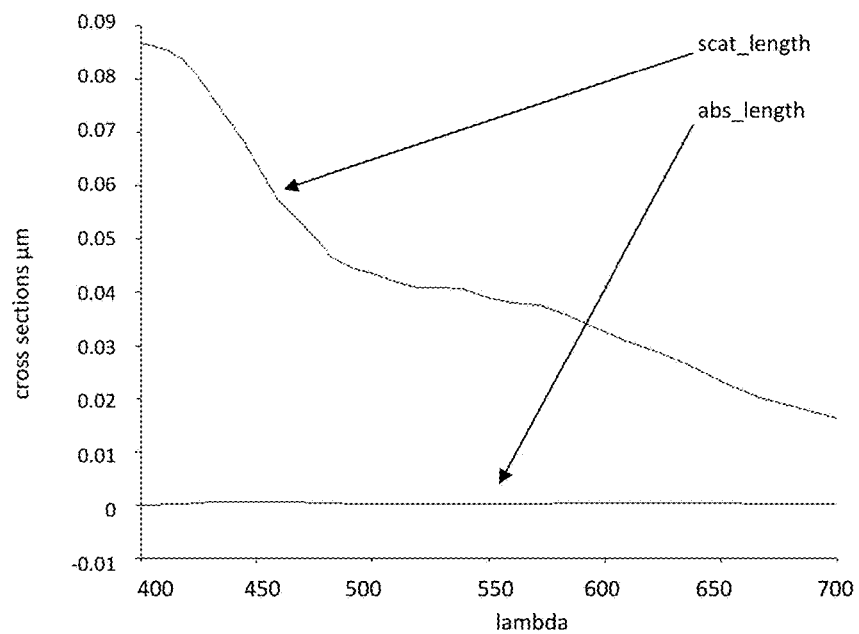
FIG. 12 shows simulated scattering cross-sections as function of wavelength of a microstructure for use in a light coupler, according to example embodiments.

Thus, the distribution P(r) can be determined by this model for the out-coupling power distribution R shown in FIG. 8. For example, the distribution P(r) over a part 103 of a light coupler according to embodiments, shown in FIG. 9, is illustrated in FIG. 10. Therefore, in order to obtain an out-coupled power distribution that approximates a point source, as shown in FIG. 8, a power distribution gradient P(r), ranging from high 105 to low 104, may be provided in the coupler as shown in FIG. 10. Since the out-coupling power distribution R is also related to the scattering cross-section and scatter density, as follows:

$$\frac{dP(r)}{dr} = -\frac{1}{r}P(r) - n\sigma P(r);$$

a target scatterer density n can be defined when the cross-section σ is known. This cross-section can for example be obtained by simulation, e.g. using lumerical. For example, FIG. 11 shows a simulation model, comprising a mode source 110 and a microstructure acting 111 as scatterer, e.g. a shallow etch. The model also comprises a field monitoring box 112 for measuring the scattering field in order to calculate the simulated scattering cross-section. The simulated model uses a SiN 113 on SiO$_2$ 114 platform. FIG. 12 shows example simulation results of the scattering cross-section σ as function of the wavelength λ.

Figure 13:
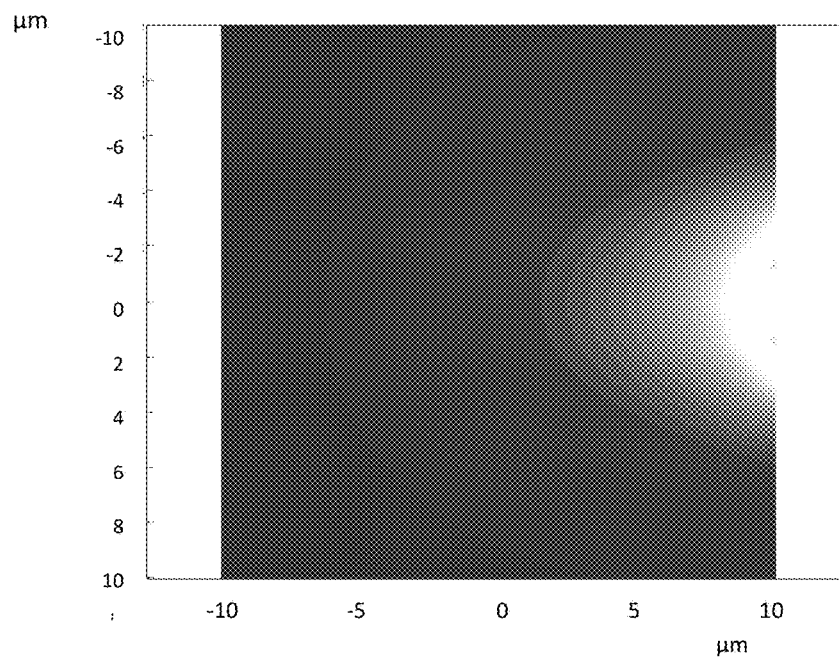
FIG. 13 shows a target distribution of scattering microstructures for use in a light coupler, according to example embodiments.
Figure 14:
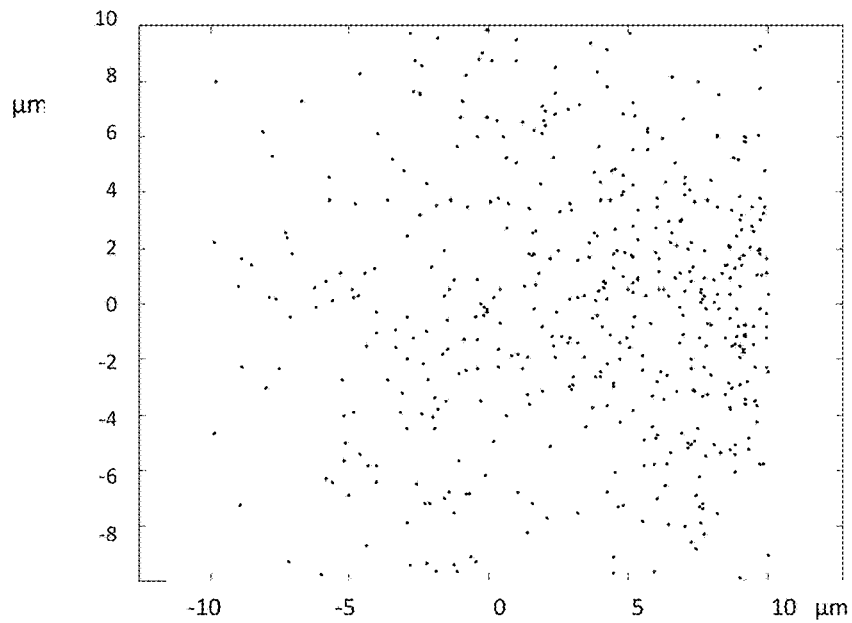
Figure 15:
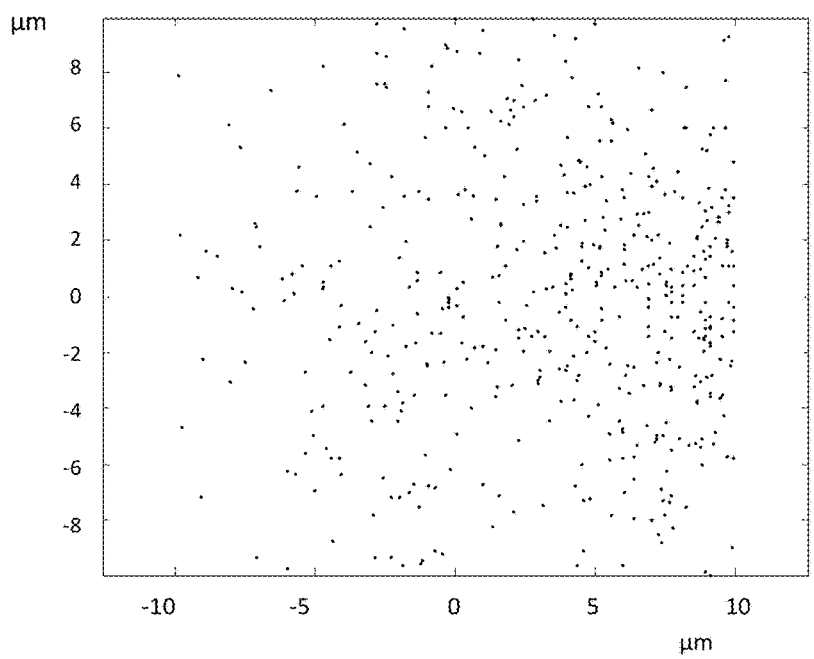
FIG. 15 shows a random sampling of scattering microstructure locations from a target distribution of scattering microstructures for use in a light coupler, wherein these randomly sampled locations are adjusted such as to fall on the nearest grating line, according to example embodiments.

FIG. 13 shows an example distribution n of scattering centers corresponding to the example simulation results shown in FIG. 12 and the target power distribution P shown in FIG. 10, in accordance with the mathematical relation hereinabove. This distribution can for example be used to randomly sample positions for the microstructures to be fabricated in the waveguide in accordance with embodiments, e.g. as shown in FIG. 14. Furthermore, the position of each such randomly sampled location may be adjusted such as to fall on the nearest grating line, e.g. as shown in FIG. 15.

Figure 16:
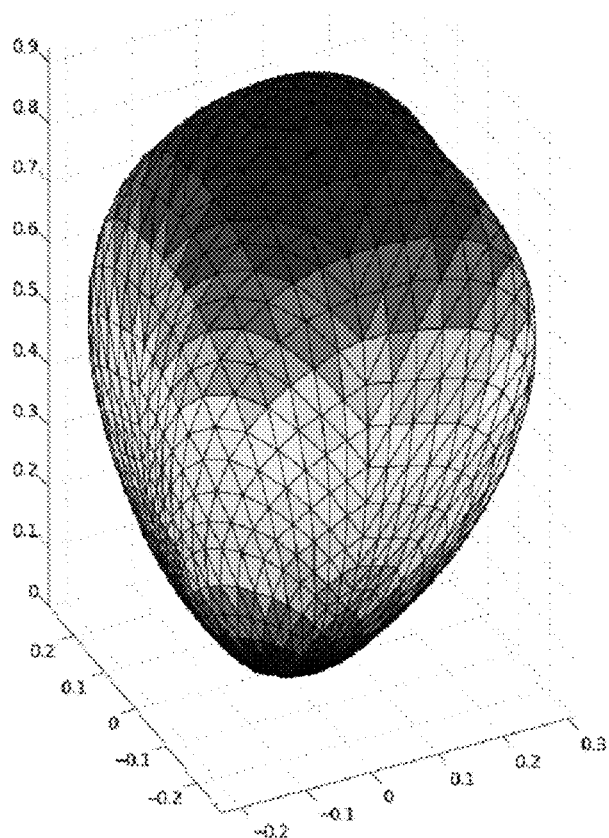
FIG. 16 shows an iso-intensity surface of scattered light obtained by a simulation of a light coupler, according to example embodiments.
Figure 17:
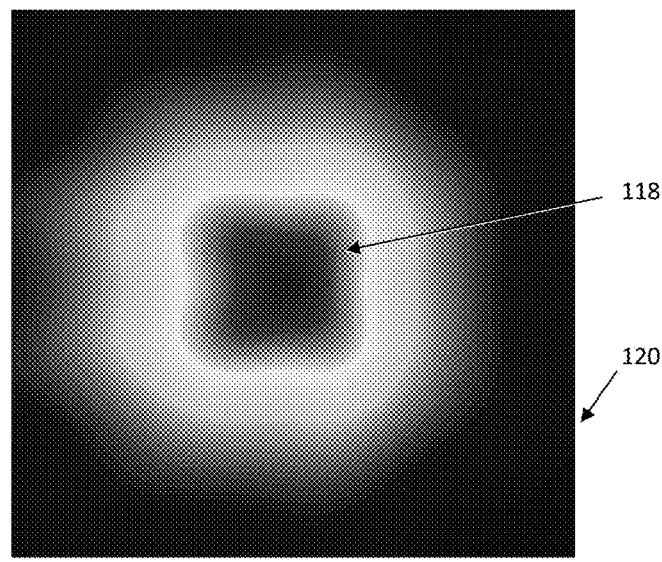
FIG. 17 shows a scattering intensity plot of a simulation of a light coupler according to example embodiments.
Figure 18:
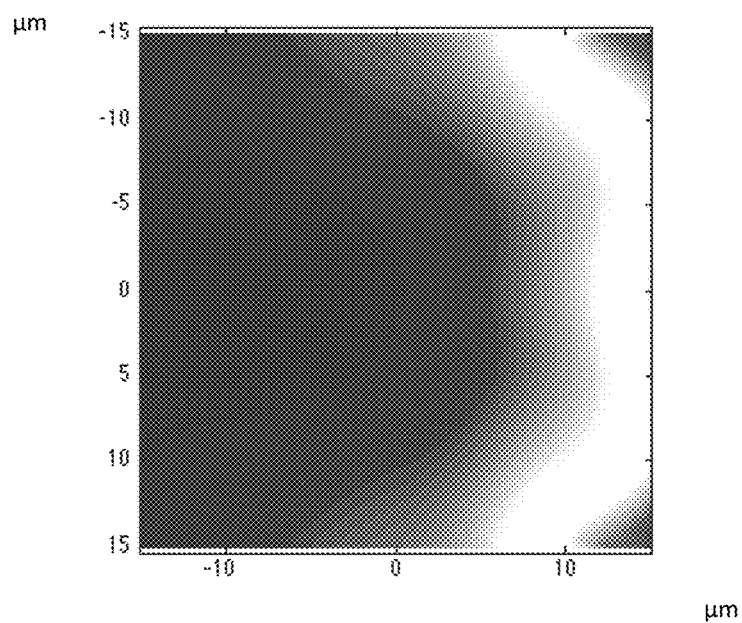
FIG. 18 shows a target distribution for scattering center locations in which anisotropy of the scattering microstructures is taken into account, according to example embodiments.
Figure 19:
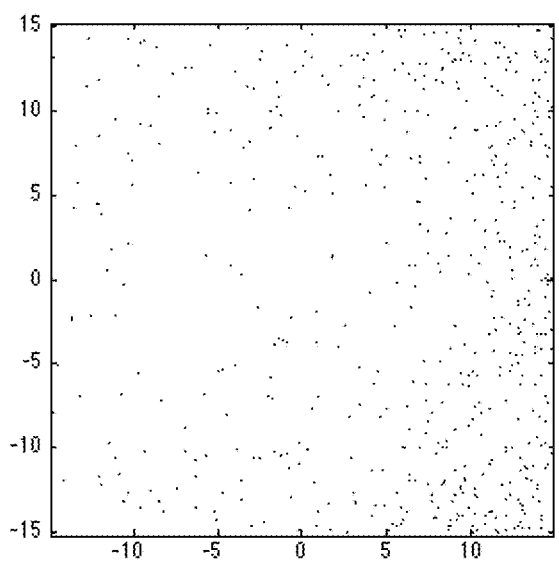
FIG. 19 shows a random sampling of microstructures in accordance with a target density distribution compensated for anisotropic scattering of the microstructures, according to example embodiments.
Figure 20:
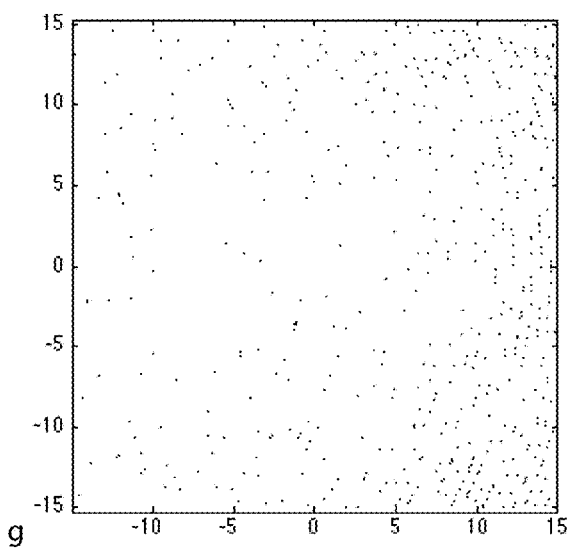
FIG. 20 shows a random sampling of microstructures in accordance with a target density distribution compensated for anisotropic scattering of the microstructures, wherein the randomly sampled microstructure locations are adjusted to the nearest position on a grating line, according to example embodiments.

Since the scatterer may be not isotropic, anisotropic scattering may also be taken into account. FIG. 16 shows an iso-intensity surface of scattered light obtained by a simulation. FIG. 17 shows a 2D scattering intensity plot of the same simulation, showing the decreasing intensity of scattering from a central area 118 to a peripheral area 119 of the microstructure. For example, an anisotropy induced by the rectangular shape of the modelled microstructure etch can be seen on FIGS. 16 and FIG. 17. FIG. 18 shows an example distribution n for the scattering centers, after taking such anisotropy of the microstructures into account. FIG. 19 and FIG. 20 show respectively a random sampling of microstructures in accordance with this distribution n compensated for the anisotropic scattering of the microstructures, and these randomly sampled microstructure locations adjusted to the nearest position on a grating line.

Figure 21:
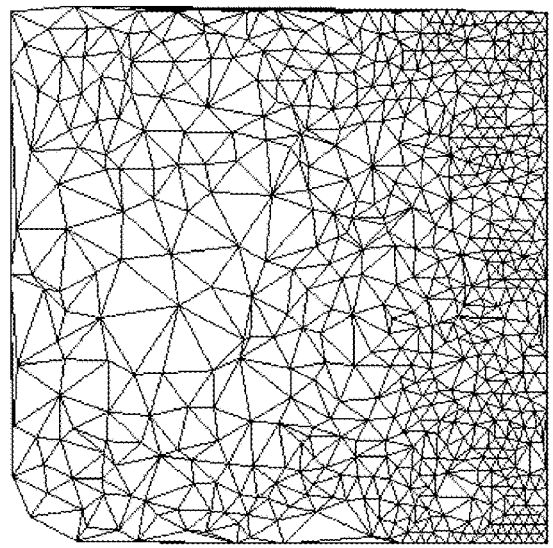
FIG. 21 illustrates a mesh for iteratively improving the conformity of a simulated light coupler, according to example embodiments.
Figure 22:
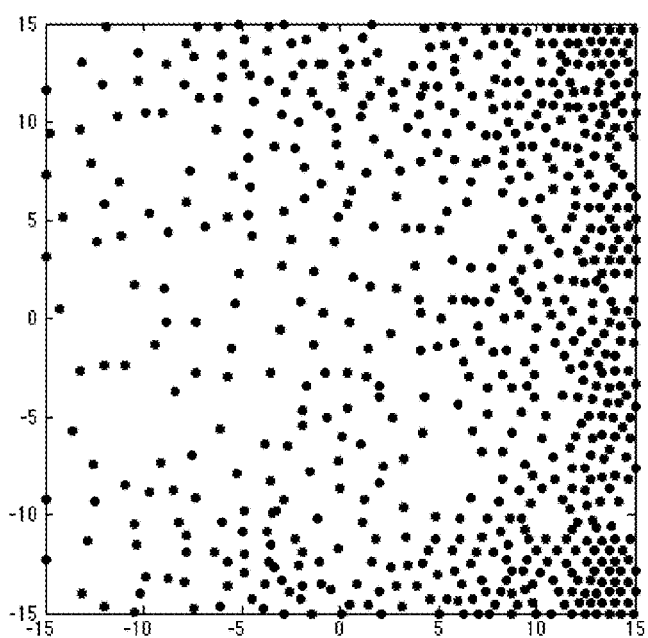
FIG. 22 shows a first positioning of scattering microstructures in a simulated light coupler corresponding to an iteration in a iterative mesh optimization simulation, according to example embodiments.
Figure 23:
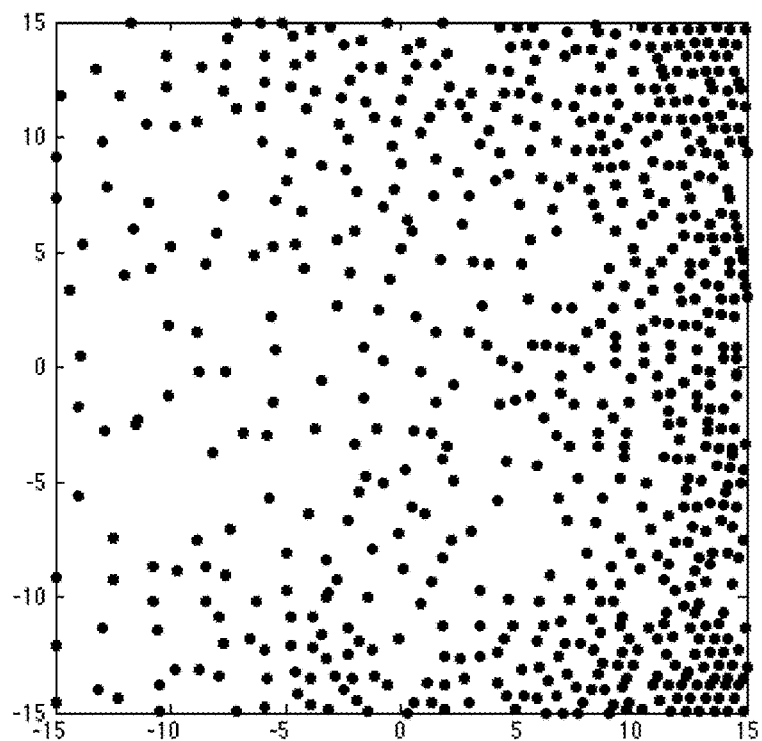
FIG. 23 shows a second positioning of scattering microstructures in a simulated light coupler corresponding to another iteration in an iterative mesh optimization simulation, according to example embodiments.

Furthermore, the conformity of the grating coupler for providing an approximated point source may be further improved by using meshing tools, e.g. to adjust the spacing between microstructure locations, for example obtained by an initial random sampling as discussed hereinabove, so as to improve a simulated out-coupled field conformity to the target point source distribution in each iteration. FIG. 21 illustrates such mesh, while FIG. 22 and FIG. 23 illustrate the microstructure positioning in two mesh correction iterations.

Figure 24:
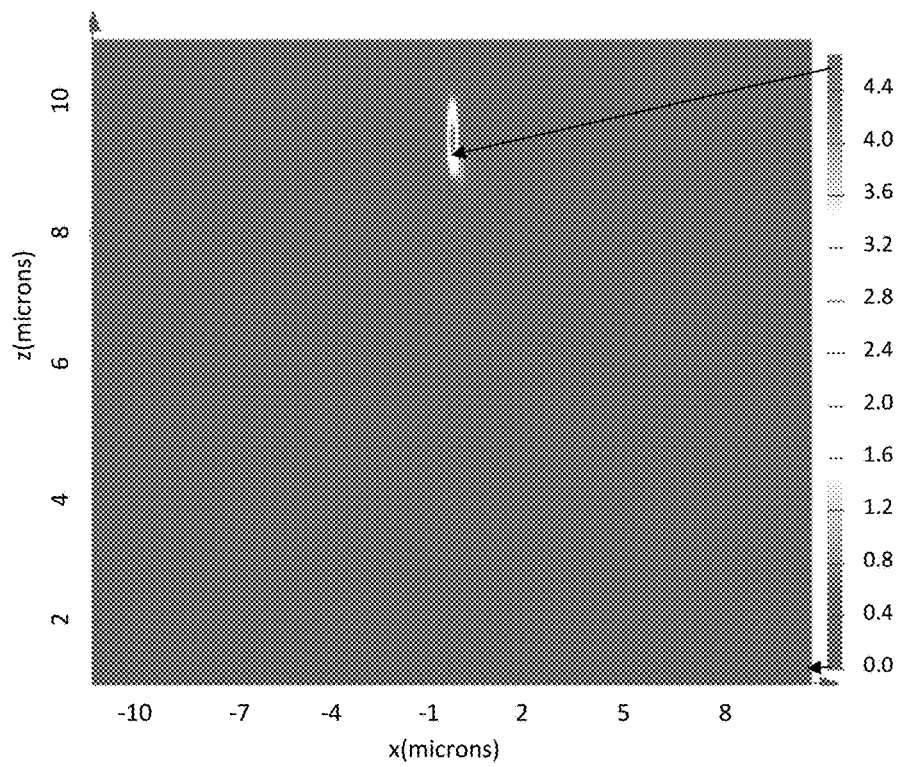
FIG. 24 shows a simulated out-coupled light field of a light coupler, illustrating the focal spot formed at a focal distance above the plane of the coupler, according to example embodiments.
Figure 25:
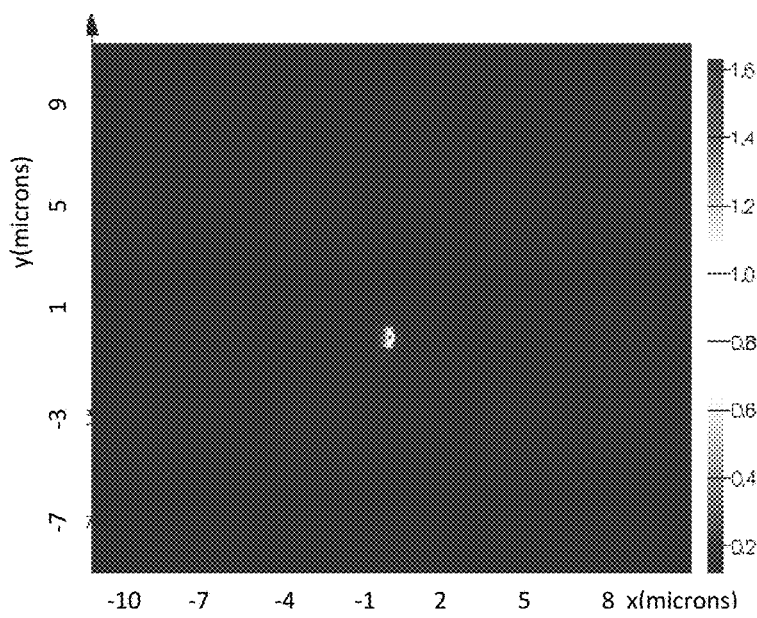
FIG. 25 shows a simulated out-coupled light field of a light coupler, illustrating the focal spot in a focal plane parallel to the plane of the coupler, according to example embodiments.
Figure 26:
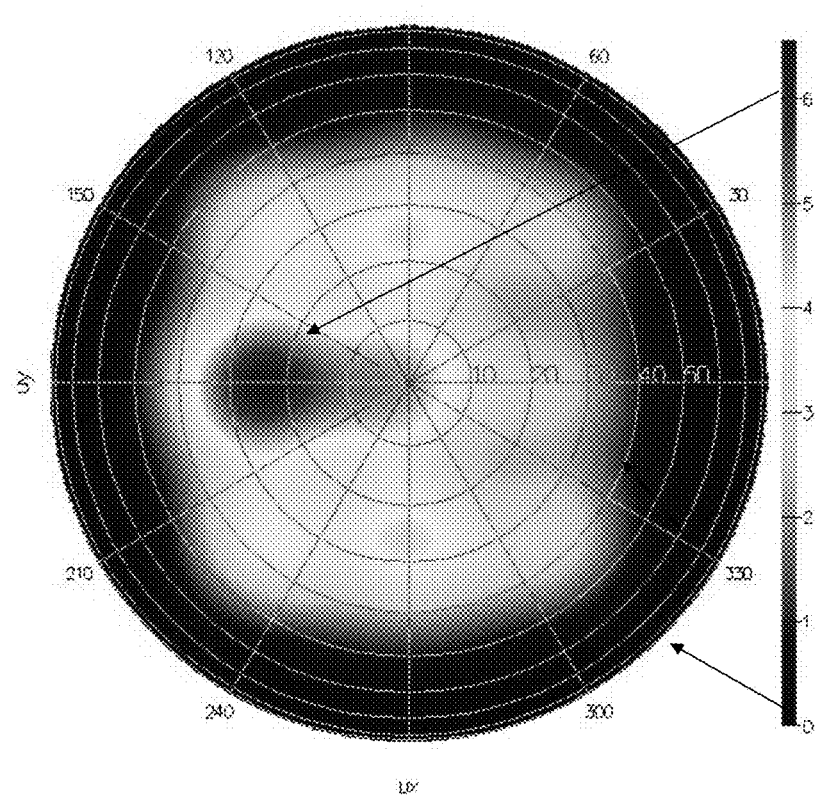
FIG. 26 shows the far field of out-coupled light of a simulated light coupler according to example embodiments.

FIGS. 24 to 26 show a simulated field above a light coupler that comprises microstructures as obtained by a procedure described hereinabove. The simulated coupler has dimensions 10 μm by 10 μm in the z=0 plane of the simulation coordinate system. The coupler was designed to provide a focus at a distance of 10 at (x,y,z)=(0,0,10) μm. FIG. 24 shows the focal spot formed at this distance above the coordinate system origin. FIG. 25 shows the focal spot of about 250 nm formed in the focal plane. FIG. 26 shows the far field of the light coupled out of the waveguide by the grating coupler.

The invention claimed is:

1. An imaging device comprising:
   at least one photonic integrated circuit comprising:
      an integrated waveguide for guiding a light signal; and
      a light dispersing structure optically coupled to the integrated waveguide,
      wherein the light dispersing structure is a light propagating region in the photonic integrated circuit, and
      wherein the light dispersing structure is configured to radiate the light signal out of a plane of the photonic integrated circuit as a light beam;
   a microfluidic channel for containing an object immersed in a fluid medium, wherein the microfluidic channel is configured to enable, in operation of the imaging device, illumination of the object by the light beam; and
   at least one imaging detector positioned for imaging the object illuminated by the light beam on an opposite side of the microfluidic channel from the light dispersing structure.

2. The imaging device according to claim 1, wherein the light dispersing structure is a focusing light dispersing structure adapted for focusing the light signal out of the plane of the photonic integrated circuit as a focused light beam converging in a focal plane.

3. The imaging device according to claim 2,
   wherein the focusing light dispersing structure comprises a pattern of microstructures fabricated in the integrated waveguide, and wherein the pattern of microstructures is adapted to compensate decay of a light signal propagating in the focusing light dispersing structure.

4. The imaging device according to claim 1,
wherein the at least one photonic integrated circuit further comprises at least one additional light dispersing structure optically coupled to the integrated waveguide,
wherein the at least one additional light dispersing structure is a light propagating region in the photonic integrated circuit,
wherein the at least one additional light dispersing structure is configured to radiate the light signal out of the plane of the photonic integrated circuit as a light beam, and
wherein the light dispersing structure and the at least one additional light dispersing structure are positioned such that light beams respectively generated by the light dispersing structure and the at least one additional light dispersing structure simultaneously illuminate the object from different angles.

5. The imaging device according to claim 1, further comprising a reflective surface, wherein the reflective surface and the at least one imaging detector are positioned such that light from the illuminated object and the light beam is reflected by the reflective surface and detected by the at least one imaging detector after reflection.

6. The imaging device according to claim 1, further comprising at least one pinhole positioned in between the at least one photonic integrated circuit and the at least one imaging detector for spatially filtering the light beam.

7. The imaging device according to claim 1, further comprising an excitation waveguide, wherein the integrated waveguide of the at least one photonic integrated circuit is optically coupled to the excitation waveguide via a waveguide splitter.

8. The imaging device according to claim 4,
wherein the at least one imaging detector is adapted for simultaneously imaging a plurality of objects, and
wherein each object is positioned such that each object is illuminated by a different light dispersing structure.

9. The imaging device according to claim 1, wherein the integrated waveguide is optically coupled to different parts of the light dispersing structure, thereby increasing uniformity of the light beam.

10. The imaging device according to claim 1, further comprising an at least partially coherent light source for providing the light signal to the at least one photonic integrated circuit.

11. A method for imaging an object, the method comprising:
coupling a light signal into an integrated waveguide;
generating a light beam from the light signal using a light dispersing structure, wherein the light beam is directed out of a plane of the integrated waveguide, and wherein the light dispersing structure is a light propagating region in a photonic integrated circuit;
transporting the object by immersing the object in a fluid that flows in a microfluidic channel;
illuminating the object with the light beam; and
imaging the illuminated object on an opposite side of the microfluidic channel from the light dispersing structure.

12. The method according to claim 11, wherein the light dispersing structure is a focusing light dispersing structure, and wherein the method further comprises focusing the light beam using the light dispersing structure.

13. The method according to claim 12, further comprising spatially filtering the light beam in a focal spot thereof, thereby obtaining a substantially uniform spherical wave propagating from the focal spot toward the object.

14. The method according to claim 11,
wherein the steps of claim 11 are performed in parallel for a plurality of objects using a respective plurality of integrated waveguides and a respective plurality of light dispersing structures,
wherein the light signal is coupled into the respective plurality of integrated waveguides, and
wherein imaging the illuminated objects comprises simultaneously imaging a plurality of objects, each object illuminated by a light beam generated by a respective light dispersing structure.

15. The method according to claim 11, wherein the light signal is an at least partially coherent light beam.

16. A photonic integrated circuit comprising:
an integrated waveguide for guiding a light signal; and
a light dispersing structure optically coupled to the integrated waveguide, wherein the light dispersing structure is a light propagating region in the photonic integrated circuit,
wherein the light dispersing structure is configured to radiate the light signal out of a plane of the photonic integrated circuit as a light beam,
wherein a microfluidic channel for containing an object immersed in a fluid medium is arranged relative to the photonic integrated circuit so as to enable illumination of the object by the light beam,
wherein at least one imaging detector is arranged relative to the microfluidic channel for imaging the object illuminated by the light beam, and
wherein the at least one imaging detector is positioned on an opposite side of the microfluidic channel from the light dispersing structure.

17. The photonic integrated circuit according to claim 16, wherein the light dispersing structure is a focusing light dispersing structure adapted for focusing the light signal out of the plane of the integrated waveguide as a focused light beam converging in a focal plane.

18. The photonic integrated circuit according to claim 17,
wherein the focusing light dispersing structure comprises a pattern of microstructures fabricated in the integrated waveguide, and
wherein the pattern of microstructures is adapted to compensate decay of a light signal propagating in the focusing light dispersing structure.

19. The photonic integrated circuit according to claim 16, further comprising at least one additional light dispersing structure optically coupled to the integrated waveguide,
wherein the at least one additional light dispersing structure is a light propagating region in the photonic integrated circuit,
wherein the at least one additional light dispersing structure is configured to radiate the light signal out of the photonic integrated circuit as a light beam, and
wherein the light dispersing structure and the at least one additional light dispersing structure are positioned such that light beams respectively generated by the light dispersing structure and the at least one additional light dispersing structure simultaneously illuminate the object from different angles.

20. The photonic integrated circuit according to claim 16, wherein the integrated waveguide is optically coupled to different parts of the light dispersing structure, thereby increasing uniformity of the light beam.

\* \* \* \* \*